(12) United States Patent
Laitsaari et al.

(10) Patent No.: US 11,597,276 B2
(45) Date of Patent: Mar. 7, 2023

(54) DEVICE, A METHOD, AND A COMPUTER PROGRAM FOR DETERMINING THE DRIVING BEHAVIOR OF A DRIVER

(71) Applicant: Taipale Telematics Oy, Tampere (FI)

(72) Inventors: Juha Laitsaari, Hämeenlinna (FI); Antti Torpo, Tampere (FI)

(73) Assignee: Taipale Telematics Oy, Tampere (FI)

( * ) Notice: Subject to any disclaimer, the term of this patent is extended or adjusted under 35 U.S.C. 154(b) by 0 days.

(21) Appl. No.: 17/674,434

(22) Filed: Feb. 17, 2022

(65) Prior Publication Data
US 2022/0266691 A1      Aug. 25, 2022

(30) Foreign Application Priority Data

Feb. 19, 2021    (FI) ...................................... 20215174

(51) Int. Cl.
*B60K 28/02* (2006.01)
*A61B 5/02* (2006.01)
(Continued)

(52) U.S. Cl.
CPC .............. *B60K 28/02* (2013.01); *A61B 5/024* (2013.01); *A61B 5/0205* (2013.01);
(Continued)

(58) Field of Classification Search
CPC .............. B60K 28/02; B60K 2028/003; B60K 2031/0091; B60K 28/10; B60K 31/00;
(Continued)

(56) References Cited

U.S. PATENT DOCUMENTS 4,439,824 A    3/1984  Mayer
9,956,963 B2 * 5/2018  Vijaya Kumar ...... B60W 40/08
(Continued)

FOREIGN PATENT DOCUMENTS

EP       3006297 A1    4/2016
FI        120474 B    10/2009
JP      2015110417 A   6/2015

OTHER PUBLICATIONS

Office Action of corresponding Finnish Application No. 20215174, dated Feb. 25, 2021, 3 pages.
(Continued)

*Primary Examiner* — Tyler J Lee
(74) *Attorney, Agent, or Firm* — Meunier Carlin & Curfman LLC (57) ABSTRACT

The invention relates to a device for determining the driving behavior of a driver, the device comprising at least means for receiving data from two or more data sources, of which at least one produces data relating to changes in the state of motion of a vehicle and at least one other produces measured data on the well-being of the driver; means for scoring the received data by comparing it with data-specific reference values; means for forming a respective sub-index from each scored item of data; means for determining a driving behavior index on the basis of the formed sub-indices; and means for controlling control equipment of the vehicle on the basis of the driving behavior index and/or for storing the driving behavior index in a database.

15 Claims, 4 Drawing Sheets

(51) Int. Cl.
| | |
|---|---|
| *A61B 5/11* | (2006.01) |
| *B60K 28/10* | (2006.01) |
| *B60K 31/00* | (2006.01) |
| *B60Q 9/00* | (2006.01) |
| *G07C 5/02* | (2006.01) |
| *G07C 5/08* | (2006.01) |
| *A61B 5/0205* | (2006.01) |
| *A61B 5/024* | (2006.01) |
| *A61B 5/145* | (2006.01) |
| *A61B 5/16* | (2006.01) |
| *A61B 5/18* | (2006.01) |
| *A61B 5/00* | (2006.01) |
| *G08G 1/0967* | (2006.01) |
| *B60K 28/00* | (2006.01) |

(52) U.S. Cl.
CPC ........ *A61B 5/1118* (2013.01); *A61B 5/14542* (2013.01); *A61B 5/165* (2013.01); *A61B 5/18* (2013.01); *A61B 5/4806* (2013.01); *A61B 5/4875* (2013.01); *B60K 28/10* (2013.01); *B60K 31/00* (2013.01); *B60Q 9/00* (2013.01); *G07C 5/02* (2013.01); *G07C 5/085* (2013.01); *G08G 1/096766* (2013.01); *A61B 2503/22* (2013.01); *B60K 2028/003* (2013.01); *B60K 2031/0091* (2013.01)

(58) Field of Classification Search
CPC ..... A61B 5/0205; A61B 5/024; A61B 5/1118; A61B 5/14542; A61B 5/165; A61B 5/18; A61B 5/4806; A61B 5/4875; A61B 2503/22; G08G 1/096766; B60Q 9/00; G07C 5/02; G07C 5/085
See application file for complete search history.

(56) References Cited

U.S. PATENT DOCUMENTS

| | | | |
|---|---|---|---|
| 10,196,071 B1 | 2/2019 | Rowson et al. | |
| 10,262,219 B2* | 4/2019 | Kim | G06V 20/597 |
| 10,379,535 B2* | 8/2019 | Migneco | A61B 5/746 |
| 10,780,880 B2* | 9/2020 | Wood | B60W 30/09 |
| 10,836,403 B2* | 11/2020 | Migneco | B60W 50/085 |
| 10,867,218 B2* | 12/2020 | Gallagher | B60R 25/25 |
| 2013/0164715 A1* | 6/2013 | Hunt | G09B 9/052 434/65 |
| 2014/0180557 A1* | 6/2014 | Hunt | B60W 40/076 701/99 |
| 2016/0046298 A1* | 2/2016 | DeRuyck | G06V 20/597 340/576 |
| 2016/0052391 A1* | 2/2016 | Walsh | G08B 21/06 340/575 |
| 2016/0090097 A1* | 3/2016 | Grube | G08B 21/06 340/576 |
| 2016/0244067 A1* | 8/2016 | Hunt | B60W 30/143 |
| 2016/0287158 A1* | 10/2016 | Lawrenson | B60K 28/06 |
| 2016/0362118 A1 | 12/2016 | Mollicone et al. | |
| 2017/0202501 A1 | 7/2017 | Kuwahara et al. | |
| 2017/0355377 A1* | 12/2017 | Vijaya Kumar | B60W 50/0098 |
| 2018/0197440 A1 | 7/2018 | Ramachandra et al. | |
| 2018/0281808 A1 | 10/2018 | Minegishi et al. | |
| 2018/0326966 A1 | 11/2018 | Li et al. | |
| 2019/0210591 A1* | 7/2019 | Low | B60W 30/02 |
| 2019/0367029 A1 | 12/2019 | Martinez Ruvalcaba et al. | |
| 2019/0375409 A1 | 12/2019 | Hunt et al. | |
| 2021/0039644 A1 | 2/2021 | Magolan et al. | |
| 2021/0169417 A1* | 6/2021 | Burton | A61B 5/4857 |

OTHER PUBLICATIONS

European Search Report for corresponding application EP22152704 dated Jul. 4, 2022.

Finnish Search Report dated Sep. 1, 2021, in FI Patent Application No. 20215174, 8 pages.

Notification of Allowance dated Oct. 25, 2021, in FI Patent Application No. 20215174, 30 pages.

* cited by examiner

DEVICE, A METHOD, AND A COMPUTER PROGRAM FOR DETERMINING THE DRIVING BEHAVIOR OF A DRIVER

CROSS-REFERENCE TO RELATED APPLICATIONS

This application claims priority under 35 USC § 119 to Finnish Patent Application No. 20215174 filed on Feb. 19, 2021.

FIELD OF THE INVENTION

The invention relates to a device for determining the driving behavior of a driver and for calculating a driving behavior index indicating the same. Furthermore, the invention relates to a method and a computer program to be executed in the device.

BACKGROUND OF THE INVENTION

The state and condition of a driver of a vehicle are important factors affecting safe driving. For detecting a decrease in alertness and for detecting use of drugs or alcohol, devices are available by which the driver can be instructed to take a break or, in an extreme situation, prevented from starting of the vehicle.

By said devices, factors affecting the driver's capability to drive are monitored during driving or right before starting to drive. Moreover, such devices are used for looking merely at a single factor affecting the capability to drive. Therefore, existing devices are not capable of making an overall assessment of the driver's driving behavior, considering not only the condition during driving but also factors having a more general impact on the person's driving performance.

BRIEF SUMMARY OF THE INVENTION

The present invention addresses the above presented problem and discloses an improved device for determining the driving behavior of a driver of a vehicle and for calculating a driving behavior index indicating the same. Furthermore, the invention relates to a method and a computer program to be executed in said device.

According to an example, the device for determining the driving behavior of a driver of a vehicle comprises at least means for receiving data from two or more data sources, of which at least one produces data relating to changes in the state of motion of the vehicle and at least one other generates measured data on the well-being of the driver; means for scoring the received data by comparing it with data-specific reference values; means for forming a respective sub-index from each scored item of data; means for determining a driving behavior index on the basis of the formed sub-indices; means for controlling control equipment of the vehicle on the basis of the driving behavior index and/or for storing the driving behavior index in a database.

According to another example, the method to be executed by a computer comprises steps of receiving data from two or more data sources, of which at least one produces data relating to changes in the state of motion of the vehicle, and at least one other produces measured data on the well-being of the driver; scoring the received data by comparing it with data-specific reference values; forming a respective sub-index from each scored item of data; determining a driving behavior index on the basis of the formed sub-indices; controlling control equipment of the vehicle on the basis of the driving behavior index; and/or storing the driving behavior index in a database.

According to another example, the computer-readable storage medium comprises computer commands which, when executed by at least one processor, make the device receive data from two or more data sources, of which at least one produces data relating to changes in the state of motion of a vehicle, and at least one other produces measured data on the well-being of the driver; score the received data by comparing it with data-specific reference values; form a respective sub-index from each scored item of data; determine a driving behavior index on the basis of the formed sub-indices; control control equipment of the vehicle on the basis of the driving behavior index; and/or store the driving behavior index in a database.

According to an embodiment, data from two or more data sources comprises one or more of the following items:
location data;
data obtained from the control equipment of the vehicle;
traffic data;
weather/road condition data;
operational control data;
aggregated data on movements of the driver.

In an embodiment of the invention, data on well-being comprises one or more of the following items:
heart rate data;
sleep data;
alertness;
stress level;
oxygen saturation;
activity level;
body temperature;
moisture content.

According to an embodiment, the device has a data connection to a starting system of the vehicle, for transmitting a start inhibit command on the basis of the driving behavior index.

According to an embodiment, the device has a data connection to a speed control system of the vehicle, for transmitting a speed limit command on the basis of the driving behavior index.

According to an embodiment, the device comprises means for limiting driving in a specific area and/or at a specific time.

According to an embodiment, the device comprises means for transmitting messages relating to the driver's capability to drive to a well-being device, a mobile device, and/or a vehicle information display.

According to an embodiment, the device for determining the driving behavior index on the basis of the formed sub-indices is configured to determine weighting coefficients for the respective sub-indices on the basis of data obtained from other data sources.

According to an embodiment, the means for determining the driving behavior index on the basis of the formed sub-indices is configured to determine weighting coefficients for the respective sub-indices on the basis of history data.

DESCRIPTION OF THE DRAWINGS

In the following, the invention will be described in more detail with reference to the appended figures, in which.

DETAILED DESCRIPTION

The aim of the present solution is to disclose a device, a method and a computer program for determining driver-specific driving behavior, as well as a driving behavior index for indicating the same, and for controlling the functions of a vehicle on the basis of the driving behavior index.

In this text, reference is made to the terms "driving behavior" and "driving behavior index" (DBI) or "individual driving index" (IDI). Driving behavior refers to a driver-specific and recognizable combination of behaving and reacting in changing and/or recurring situations. Driving behavior is thus the driver's "fingerprint" or "individual pattern" of performing in a driving situation. Driving behavior may be misinterpreted as "capability to drive" which refers primarily to so-called driving health. Driving health is the capacity to cope with a driving situation physically and mentally. Capability to drive also encompasses resilience to stress and judgement. Neither should driving behavior be interpreted as "driving skills", which is a term referring to routine achieved by training, learning and experience. Factors of driving skills include technical routines, reaction time in various and/or surprising traffic situations, training, a keen eye for traffic, the knowledge and skills required for a licence to drive the vehicle in question. The term "driving behavior index" refers to a numerical value for the driving behavior as a whole. It can be computed by means of various parameters collected in real time. History data may also be utilized in calculating the driving behavior index. The computed driving behavior index may be utilized to make more comprehensive analyses and evaluations on the factors relating to drivers' driving behavior in various driving situations and, for example, road conditions. The aim of the driving behavior index is to indicate a driver's driving behavior at a specific time under specific conditions. In some cases, the driving behavior index may also be used for driver selection, when the system is used for selecting the best driver who is capable of driving, for example, a full trailer combination truck under snowing conditions in the dark.

As mentioned above, vehicles already comprise devices for detecting, for example, a decrease in the alertness of the driver. Such devices determine a decrease in the alertness on the basis of data obtained from e.g., cameras and relating to eye movements, as well as assessed anomalies in the driver's driving behavior. However, decreased alertness is a factor which affects the driver's capability to drive at a time and does not stand for the driver's driving behavior in general, that is, the driver's way of coping with a specific driving situation. On the other hand, alertness is a factor affecting the driving behavior, and this is why the determined data on alertness can also be utilized in determining the driving behavior index presented in this approach.

The present approach relates to a system determining the driver's driving behavior by measuring parameters relating to the driver and the driving situation in real time, as well as by utilizing history data. The driving behavior indicates the driver's way of coping with the driving situation in question. The driving behavior index indicating the driving behavior is computed by combining the driver's well-being data with other data required for measuring the driving behavior, such as data indicating the driving situation at the time. The driver's well-being data can be collected from a personal sensor arranged in a well-being device or wearable in another way, whereby the solution also encompasses cooperation and interface between the vehicle and the well-being device. In this description, the term "well-being data" covers any measurable data on a person, even if said data did not indicate well-being directly. Consequently, well-being data includes, e.g., the driver's heart rate but also the driver's movements. Other examples of well-being data are described in different examples of the description.

It is an aim of the invention to utilize data produced by existing systems for measuring and/or analyzing driving behavior, in combination with the driver's personal data and/or data produced by a personal well-being sensor in real time and/or stored data relating to a previous moment of time. The idea of the invention is thus to supplement existing driver monitoring data with personal physiological data (so-called well-being data) on the driver. Furthermore, in different embodiments of the invention, it is also possible to utilize data obtained from third parties.

Figure 1:
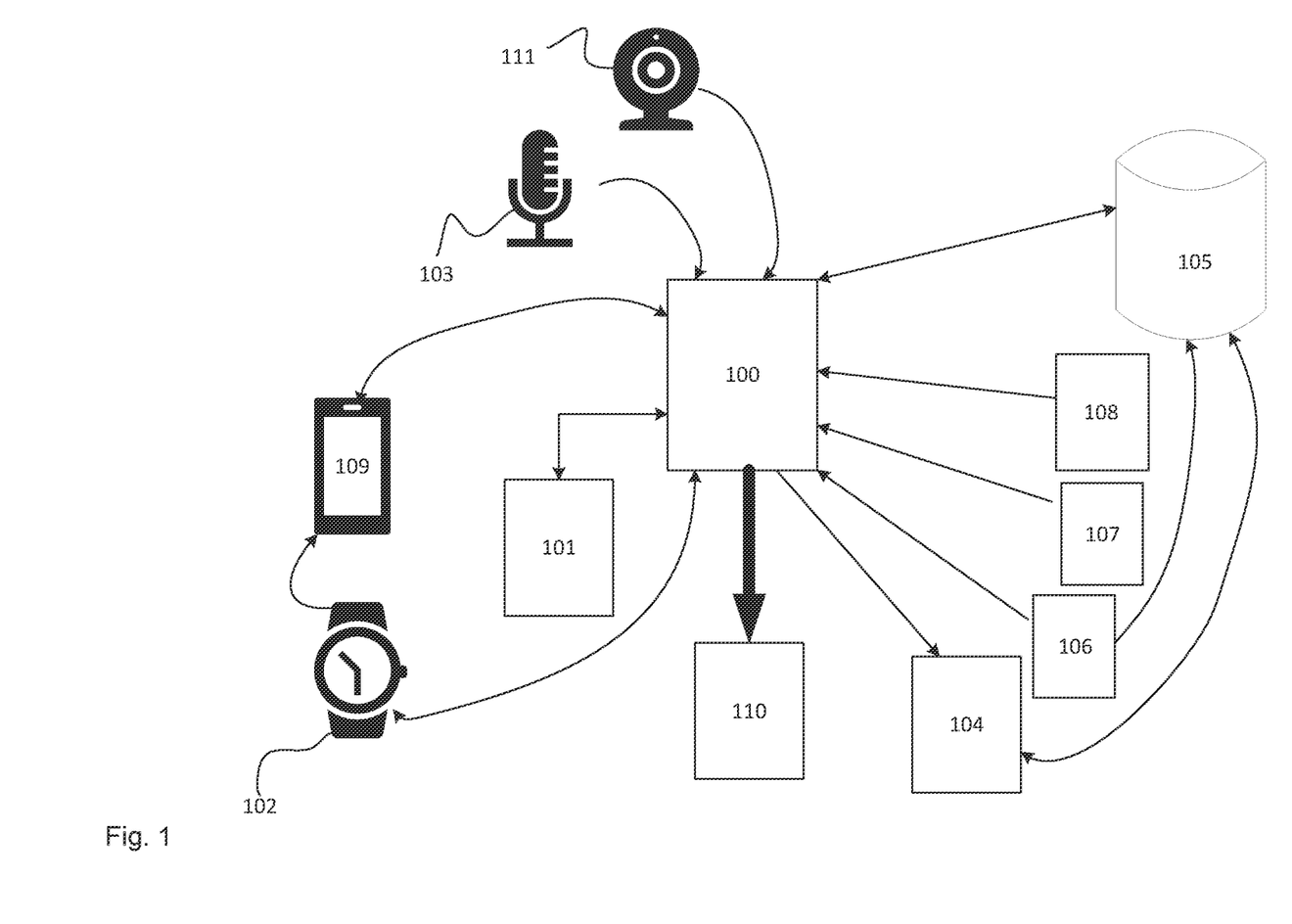
FIG. 1 illustrates an example of a system for determining the driving condition and state of a driver.
Figure 4:
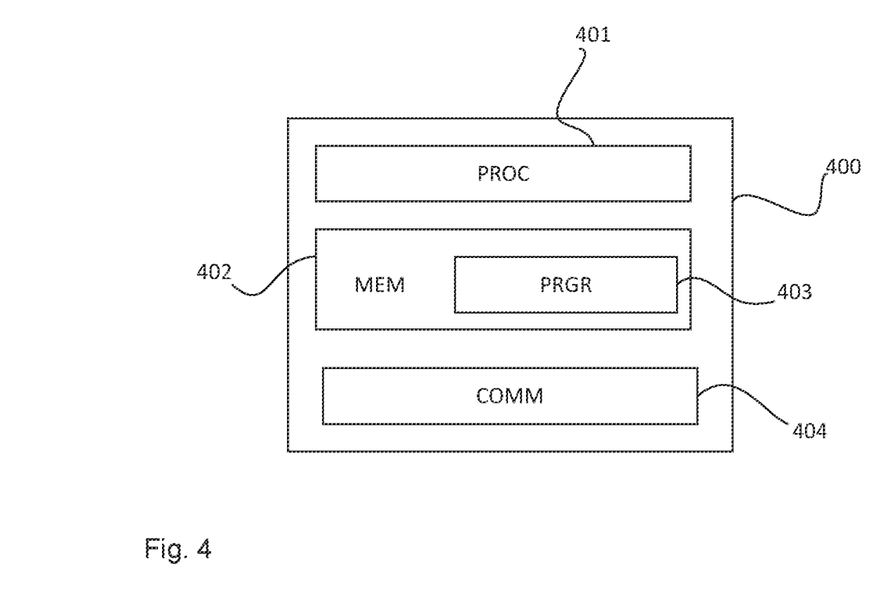
FIG. 4 shows a device according to an embodiment.

FIG. 1 shows an example of the system and the related data sources. A primary element of the invention is a driving behavior device 100 (i.e., a vehicle monitoring system). The driving behavior device 100 may be an independent device (a more detailed example is shown in FIG. 4) which comprises at least one processor and a memory, as well as computer software stored in the memory, and is arranged in a vehicle. Alternatively, the functionality of the driving behavior device 100 may also be implemented by software in a control device or another device in the vehicle.

The driving behavior device 100 is configured to collect data from various data sources. Examples of these include a bus data source 108, other vehicles 107, other external data sources 106, a driver microphone 103, a camera 111, such as a video camera, recording the driver, and a database 105. The external data source 106 may be, for example, a meteorological or road condition information service, and/or a traffic information service, or the like. In addition, the driving behavior device collects personal data from, for example, a well-being device 102 and/or a mobile device 109 of the driver. The database 105 may comprise stored history data, such as location data, speed data, acceleration data, data obtained from the systems of the vehicle and collected by driving behavior/monitoring systems, for example before the introduction of the present invention. This data in the database is supplemented with data on the driver's well-being, collected by methods of the invention, (and/or with other data relating to the driver's physiological features or body functions), and with computed driving behavior indices. The driving behavior device 100 may process the data received by it for determining a driving behavior index, and transmit the calculation results to a database 105 on a (cloud or on-premise) server. In an alternative embodiment, the driving behavior device 100 transmits the received data in the form of raw data to the database 105 which will perform data processing and determine the driving behavior index.

The data sources shown in FIG. 1 are examples of possible data sources. As data sources, it is, however, also possible to use other devices capable of monitoring the driver's capability to drive, the driving situation, the driving environment, etc. Examples of these also include a vehicle router, an on-board computer used for operation control or fare collection, or, for example, an alcohol ignition interlock device. Sources of personal data include not only a well-being device but also telephones and tablet computers. The driver's well-being device 102 may also be a smart watch, a smart ring, a fitness tracker band, or the like, comprising sensors for detecting and measuring parameters relating to a person's well-being. The driver's well-being device 102 may also be used for identifying the driver. The driver's well-being device 102 may be used for collecting data on, for example, heart rate, heartbeat intervals, oxygen saturation, alertness, activity, sleep, the temperature of the body or a body part, etc. Moreover, the driver's well-being device 102 may receive and transmit emergency calls from the driver. The driver's well-being device 102 together with a mobile device 109 may determine the driver's working hours on the basis of data obtained from the database 105, as well as verify pauses on the basis of the activity data. The driver's well-being device 102 and/or mobile device 109 may also provide the driver with information on the driving behavior and state to drive. In addition, the well-being device 102 and/or the mobile device 109 and/or the vehicle's information display may receive/transmit information and/or warnings relating to detected conditions, such as deer, road condition, weather condition, accidents, etc.

In addition, data may be collected from samples taken from the skin or breath, such as a chemical sample indicating the use of alcohol, drugs or medicines. The driver of the vehicle may also have a measuring device consisting of one or more sensors measuring the movements of the limbs. In this way, movements of the driver are included in the analysis, for example movements of the hands on the steering wheel, movements of the head, movements of the body on the seat. Movement data may be collected by means of e.g., wearable sensors as well as movement and pressure sensors in the seat. In an analysis based on movements, it is essential to detect how the movements of the driver's hands and body react to perceptions and to movements of the automobile. Furthermore, data may be collected from an eye monitoring system, such as a camera producing data on eye movements, pupils, eyebrow positions, etc. Examples of data sources of third parties include weather and road condition services, traffic data services, traffic disruption services, operation control systems, emergency response centers, etc. The vehicles' on-board systems also collect a lot of data on the driving situation which is intended to be utilized by the manufacturer of the systems of the vehicle and which can be utilized to achieve the aims of the invention. This data may consist of status and control data on various controls, such as the state of motion, status data on actuators, as well as image recognition. Such data may be collected in, for example, an on-board diagnostic (OBD) system.

The above-presented data source may produce data which is, for example:
- position data based on GPS or other positioning technology;
- the state of motion of the vehicle in an x-y-z coordinate system, in which also road condition and weather condition can be determined on the basis of accelerations and vibrations;
- speed data from e.g., a digital tachograph;
- speed changes, acceleration, rotary acceleration;
- rotational speed of the wheels, and changes therein;
- shaft balances (vehicle loading);
- power supply usage information, such as speed of rotation, torque, etc.;
- state and speed of motion of the control devices;
- outdoor data; air and road temperature, humidity, dew point, visibility;
- road surface scanning, road markings, detection of road signs;
- well-being data, such as heart rate data, stress level, activity level, sleep history, oxygen saturation, body temperature, moisture, alertness, and/or other data derivable from a well-being sensor;
- data relating to the driving position of the driver and determined from e.g., the seat and/or the steering wheel of the vehicle; data on the movements of the driver, obtained from a phone, a wristband, a watch, clothes, a ring;
- warning signs from the speech of the driver; recognizable features may include e.g., tiredness, alcohol or drugs, aggression, unalertness;
- other aspects relating to the well-being of the driver: preventing, prediction, alarms of seizures, such as diabetes, visual defects, neurological impairments;
- result of a test on the driver's ability to drive;
- data on motions and conditions obtained from other components (e.g., tyres) of the vehicle; and data on motions and conditions obtained from trailers;
- data for reducing environmental damage;
- driving distance; minimum, average and maximum values for the speed of the vehicle; maximum accelerations of the vehicle in different directions; and identification data on the driver of the vehicle;
- data on the fuel consumption of the vehicle, data on the tyre pressure of the vehicle, data on the temperature in the driver/passenger area and/or the cargo space of the vehicle, bus data transmitted by the vehicle, or control and status data on various auxiliary equipment connected to the vehicle; etc.

The driving behavior device may utilize several items of the above-mentioned data in various combinations, for determining the driving behavior index.

Data is received and transmitted over one or more communication networks by a communications interface in the device 100. The communication network to be used is set up between the driving behavior device 100 and each data source 102, 103, 105, 106, 107, 108, 109, 111. Between the different pairs of devices, various data transmission methods can be utilized, such as Bluetooth, WiFi, and/or 5G or 6G data transmission. In some cases, data may be directed from a data source first to a data collecting device which will transmit the data further to the driving behavior device 100. An example of such an arrangement is data transmission from a well-being device 102 to a mobile device 109 which will transmit the data further to the driving behavior device 100.

When received, the data is normally raw data and specific to the data source in question. To make the received data analyzable by the driving behavior device 100, the data obtained from different sources has to be converted to a commensurate format, for example by using a common data model. As a result of the harmonization, commensurate data packets are obtained. If the driving behavior device 100 does not compute the driving behavior index, the data packets are transmitted to a database 105 for processing and for determining the driving behavior index. The data packets are also stored in the database 105 for later use.

Driver-specific data relating to the evaluation of the driving and based on analyzed data, as well as decisions made on this, may be stored in the database 105. It is also possible to create statistics in the database, collected from several drivers and based on history data. The database 105 may also be used for storing driver-specific basic data relating to e.g., the driver's work shifts, driving behavior, underlying medical conditions, etc. This data may be stored in connection with the driver profile, and it may be anonymized for use by outsiders (e.g., statistics).

On the basis of the data received, the driving behavior device 100 (or the database 105) makes decisions on the driver's driving behavior by computing a driving behavior index. The driver-specific driving behavior index is stored with the parameters indicating the driving situation in the database 105. Furthermore, if the driving behavior index indicates that the driver's driving behavior is substantially impaired in the situation at hand, the driving behavior device 100 will give a notice 104 of this and possibly make a decision on interrupting the driving. The decisions are stored in the database 105 and also transmitted to the driver, for example to the well-being device 102 and/or the mobile device 109 and/or a display of the vehicle. On the basis of the driving behavior, the driving behavior device 100 may also control an external system 110, such as the vehicle's steering equipment, speed limiters, etc.

The driving behavior device 100 is also configured to give an alarm and/or a notice in real time, without/before computing the driving behavior index. Such a situation may occur when an abrupt change is detected in the data obtained from the driver's well-being sensor, relating to for example a rise in the heart rate or another occurrence indicating a change in the health, whereby the driving behavior device is configured, for example, to check on the driver, to limit the driving speed or the driving; and/or to report on the situation, for example to a driver supervisor. A real-time alarm can be given if the driver abruptly assumes an abnormal driving behavior which can be attributed to a change in the physical or mental health. The alarm can be given to a third party, such as a central station, an emergency response center, but inside the vehicle as well.

The driving behavior index is generated in a number of ways, depending on by which, what kind of, and how much data is collected on the vehicle and/or its driver. The driving behavior index may be composed by data fusion of data obtained from different data sources, with dynamically different weightings. The driving behavior indices are commensurate with each other, but in computing, it is possible to rely on statistical processing and generalizations. Statistics is utilized when a limited amount of data and/or parameters is available. The analyses may be classified and named according to the depth of the data available.

Computational results of the driving behaviour index may be presented after the driving, for example in reports and summaries, reflecting on history. In such a case, one data source may also be data collected by other systems of the vehicle. An example of such a data source is software and cloud services of automobile manufacturers, which may provide usage data and status data on, for example, controls and accessories, as well as usage data on the power source (e.g., power, torque), and failure information. Consequently, this scheme makes it possible to cooperate with automobile manufacturers and their software providers.

In addition to the driving behavior index, the system may compute other data on risk control and environmental impacts relating to transportation. Examples include precise attribution of discharges to driving performances, considering alternative fuels, as well as analysis and disclosure of safety risks relating to the performances.

A driving behavior analysis is based on the analysis of data relating to well-being and data obtained from a third party, as well as of changes in the state of motion of the vehicle. Data relating to changes in the state of motion of the vehicle is obtained from acceleration measurement by an on-board device, from satellite data, and from systems of the vehicle. Accelerations caused by forces effective on the vehicle, as well as the speed of the vehicle, and changes in it, are used as a basis for the analysis. These will be described in more detail below.

Accelerations of the vehicle can be measured by known techniques, such as a micro mechanical acceleration sensor, a gyroscope, technology based on satellite positioning, wherein a change in the velocity is computed with respect to different axes, by sensing with a three-axis accelerometer. Accelerations of the vehicle can be measured in the driving direction, broken down in six different directions: forward (acceleration), backward (braking), left (turning to the left), right (turning to the right), up (vertical movement upward), and down (vertical movement downward). From the acceleration measurement, vibration-type acceleration at the highest frequency can be filtered out by hardware and software filtering. The filtered acceleration data reflects changes in state of motion caused by driving the vehicle. Even if the filtration removes some effects of external factors on the vehicle, such as e.g., effects of the road surface, some effects and particularly the driver's reaction to them is still reflected in the measurement result.

Norms are set for allowable acceleration values for driving the vehicle. Exceeding the limit values of the norms will cause a scoring having a negative effect on the driving index; in other words, penalty marks are computed for the driver for exposing the vehicle to excessively high accelerations. The basis for the norms is a large amount of data collected from transportation over more than ten years.

The aim of using the acceleration norms is to protect passengers of the vehicle from uncomfortable and risky travelling, goods to be transported from being damaged, the vehicle itself from wearing and being damaged, and other transport users from risky driving behavior.

The norms of acceleration are two-tiered and computed for each of the six directions separately. A minor penalty mark is given for exceeding the first level of the limit values, a major penalty mark for exceeding the second level. Repeated exceeding of the second level will also cause an immediate warning to be displayed to the driver and to be transmitted to the data system. The set limit values vary slightly according to the type of the vehicle and the transporting task, as well as the needs and wishes of the customer, but primarily the limit values are within a relatively small range, within a level of travel comfort experienced as convenient by people in passenger transport as well as freight transport.

In addition to acceleration, the speed of the vehicle and changes therein are measured, either indirectly by means of the speed computed by satellite positioning of the system, or directly by means of the speed indicated by the bus data of the vehicle.

In the speed analysis, an average speed from a longer period of time as well as minimum and maximum values are determined in addition to the instantaneous speed of the vehicle. Moreover, changes in the speed are analyzed in various ways. As in the acceleration analysis, norms are set for allowable speed values for driving the vehicle. Exceeding the limit values of the norms will cause a score having a negative effect on the driving index; in other words, penalty marks are computed for the driver for exposing the vehicle to excessive speeds or changes in the speed.

The purpose of using the speed norms is to reduce fuel costs and to protect passengers and goods transported on the vehicle, the vehicle itself, and other traffic users from selecting a harmful and dangerous driving speed.

The speed norms are two-tiered as well. A lower, so-called soft limit value for continuous driving speed is set to a level according to the vehicle, the legislation and the needs of the transport company. The limit value defines the maximum speed that the driver should use in continuous driving of long distances. The limit value is compared with the average speed of the vehicle, so that the analysis does not significantly take into account instantaneous speed values exceeding the limit value. Similarly, the upper, so-called hard limit value for instantaneous speed is set to a level according to the vehicle, the legislation and the needs of the transport company. The instantaneous limit value weights the actual safe use of the vehicle, possibly at the expense of legislation. The limit value determines the speed which the driver must not exceed even momentarily, e.g., when rolling downhill, when accelerating uphill, or during overtaking. The limit value is compared with the momentary speed of the vehicle, so that the analysis will immediately respond to speeds exceeding the limit value.

For exceeding either the lower or the upper speed limit value, the penalty mark given is the higher, the higher the speeding compared with the respective limit value. A relatively lenient penalty mark is given for exceeding the lower limit value, whereas a severe penalty mark is given for exceeding the upper limit value.

Moreover, exceeding the upper limit will always cause an immediate warning to be displayed to the driver and to be transmitted to the data system.

The set limit values vary according to the local legislation, the vehicle type and the transporting task, as well as the needs and wishes of the customer. For heavy vehicles, the limit values are typically determined according to vehicle-specific restrictions, for light vehicles according to road-specific restrictions. Monitoring the compliance with road-specific, up-to-date speed limits is partly in use.

The speed analysis also processes changes in the driving speed, in addition to occurrences of exceeding the defined limit values. Changes in the speed are analyzed for small uneven changes in the driving speed during long-distance driving and for continual changes in the driving speed primarily when driving in urban zones. These analyses apply fixed predetermined limit values which cannot be set according to the vehicle or the transport company.

The aim of the analysis of uneven driving speed is to encourage the driver to drive at a steady travel speed, preferably by applying cruise control if it is available and applicable in the respective driving situation. A steady driving speed enhances a safe and smooth traffic flow by reducing unnecessary variation in speed. The analysis is only active at highway speeds. It allows very small speed variations (±2 km/h) without responding to them. Large speed variations (>±5 km/h) are also interpreted as necessary speed variations and are not responded to. Other speed variations, falling between these ranges, are interpreted as harmful, and slight penalty marks are given for them.

The aim of the analysis of varying driving speed is to encourage the driver to drive at a steady, proactive and predictable way in urban zones, as far as this is possible in each driving situation. A steady driving speed enhances a safe and smooth traffic flow by reducing unnecessary variation in speed. The analysis allows single variations in speed, such as slowing down when approaching an intersection, traffic lights or a bus stop, and accelerating again, without significantly responding to this. Only repeated clear changes in speed (>±5 km/h back and forth) within a relatively short time are interpreted as being harmful, and a penalty marking is given for them, increasing progressively from mild to severe. If it is detected that a change in speed is associated with a change in the direction of the vehicle, for example at crossroads, it is not considered harmful even when repeated.

Data on the well-being of the driver of the vehicle is measured by a personal sensor. The well-being analysis covers not only the current well-being (heart rate, stress, alertness, etc.) of the driver of the vehicle but also the long-term well-being of the driver of the vehicle (sleep data, increase/decrease in stress level, activity, etc.), whereby overall well-being can be computed with various weightings. As in the above-mentioned analyses, norms are set for allowable changes and deviations in relation to the average well-being of the driver. Exceeding the limit values of the norms will cause a marking having a negative effect on the driving behavior index; in other words, penalty marks are given for the driver for too little sleep, too high a stress level, too low alertness, etc.

The norms relating to well-being may be two or more tiered, and they may involve a number of different factors on the well-being. For example, for the heart rate, the lower limit value should be slightly higher than resting heart rate, and the upper value should be well higher than the resting heart rate. Limit values can be set for driver-specific measured values or for average values.

Irrespective of the parameter relating to well-being, a penalty mark is given for falling below the lower value as well as for exceeding the upper value, the penalty mark being the greater, the greater the deviation from the respective limit value is.

The well-being analysis further processes changes in well-being, in addition to the above-mentioned occurrences of exceeding the limit values. Examples of these include variation in heart rate or changes in stress level, particularly during driving.

The above-mentioned acceleration analysis, speed analysis and well-being analysis are examples of analyses made. It is thus obvious that analyses are also made of other data received, whereby the presented examples should not be interpreted restrictively.

In the analyses mentioned above and in other possible analyses of the invention, the decisive factor is not necessarily considered to be exceeding a given numerical value but the decisive factor is a deviation from normal under the conditions in each case. Thus, a fixed numerical value or an average value is not necessarily significant but the deviation which reflects the normal situation.

Each analysis conducted (acceleration analysis, speed analysis, well-being analysis in the examples above) produces a score from the above-mentioned measured data, which score can be compressed into several sub-indices indicating the driving behavior, such as an acceleration sub-index, a speed sub-index and a well-being sub-index. The different sub-indices may be allocated their respective weighting coefficients which may be defined permanently or dynamically, whereby the magnitude of each weighting coefficient varies according to the prevailing circumstances. In other words, if the time of day is evening and the data obtained from weather condition data indicates freezing of road surfaces, more weight is given to the speed sub-index but also to alertness.

The sub-indices are compressed (by summing/multiplying) further into a single total index indicating the driving behavior, that is, the driving behavior index. The analyzed score and the computed indices are transmitted to the data system, to be processed further.

For example, the system receives data to be used as a basis for an analysis which is compressed into sub-indices A, B, C, D. These can be summed up, with their respective weighting coefficients, resulting in the driving behavior index, for example $A*z+B*y+C*d+D*e=DBI$. The parameters z, y, d, and e are said weighting coefficients whose value is determined dynamically from history data and/or according to the situation.

On the basis of the driving behavior index, it is possible to determine the current driving behavior of the driver. Thus, weight is attached to real-time data obtained from the well-being device as well as to well-being data stored earlier. For example, if the data obtained from the well-being device indicates that the driver of the vehicle has not slept well (qualitatively or quantitatively) several nights in succession, and the duty roster obtained from the data base indicates that the driver is facing a long work shift, the system may determine that the driver's state to drive is impaired, whereby the system may instruct the driver to take a break more often or once for a longer time.

The driving behavior index or data on the effect of the driving behavior index on the driver's performance may be transmitted to supervisory staff and/or, for example, to an occupational health centre, for measures and decisions.

Furthermore, notices may be given on the basis of the driving behavior index, and if the driving behavior index does not improve significantly, driver restrictions may be imposed by defining an allowable speed to be used and/or by defining allowable routes, or if the driving behavior index indicates that the current driving of the driver meets the criteria of risk driving, the driving may be gradually interrupted, etc.

In addition, real-time observations on changes in health, affecting the driver's driving behavior, may cause restrictions on the driving speed, the driving zone, or the driving time.

The driving behavior index (DBI), together with summaries and analyses based on it, may be supplied to the provider of another fleet management service. For example, the driving behavior index may be used for determining user fees based on performance, insurances, maintenance services, emergency calls, as well as data relating to shared e use, leasing, and charging. However, it is obvious that these are examples of possible uses of the driving behaviour index and they should thus not be interpreted to unnecessarily restrict the invention.

The numerical value of the driving behavior index may be, for example, between 0 and 100. For example, a relative driving behavior index may be determined in such a way that the best performance in a reference group is denoted by 100, and other performances below it fall in a scale from 0 to 100 or from 40 to 100. The relative driving behavior index may also be determined on the basis of the average for a reference group, which is denoted by 50, whereby the other indices range from 0 to 50 and from 50 to 100.

The driving behavior index may be applied to restrict driving, for example, so that a good driver is allowed more decision-making power and freedom, for example in view of speeds. In addition, unnecessary giving of hints is avoided. Correspondingly, for a driver having a low driving behavior index, the speed and options are restricted, and the number of instructions to be given is increased.

The driving behavior index may also be used for adjusting driving software of the vehicle. Driving software may be provided in different categories, such as "Newcomer", "Normal", "Sport", and their selection may be controlled by the driving behavior index, for example by restricting acceleration.

For computing the driving behavior index, the driving behavior device 100 may utilize machine learning, deep learning, neural networks, or other solutions providing artificial intelligence 101. Thus, for example data on the well-being of the driver and data obtained from other sources is supplied as input to the algorithm providing artificial intelligence, and on the basis of this data, the artificial intelligence solution 101 determines the driver's driving behaviour in the respective weather conditions (for example, foggy, rainy, dark), with the driver's capacity at the time (good sleep quality, alert and active mind), and/or how a decrease in a physiological parameter will affect the capability to drive at the time. The artificial intelligence solution 101 is also capable of determining weighting coefficients effective on the driving behavior index.

To make the algorithm 101 providing artificial intelligence capable of operating in a desired way and making decisions on the driver's driving behavior at the time, the machine learning algorithm has to be trained with data from which the driving situations and the environmental and well-being parameters effective on them can be derived. The machine learning algorithm may be trained with data in a database before the algorithm is taken into use, but training is also implemented during the use of the driving behavior device, on the basis of data received continually. If an accident or a near miss occurs in a driving situation, training data can be strengthened on the basis of such data, whereby the driving situation that affected the event will be registered.

Figure 2:
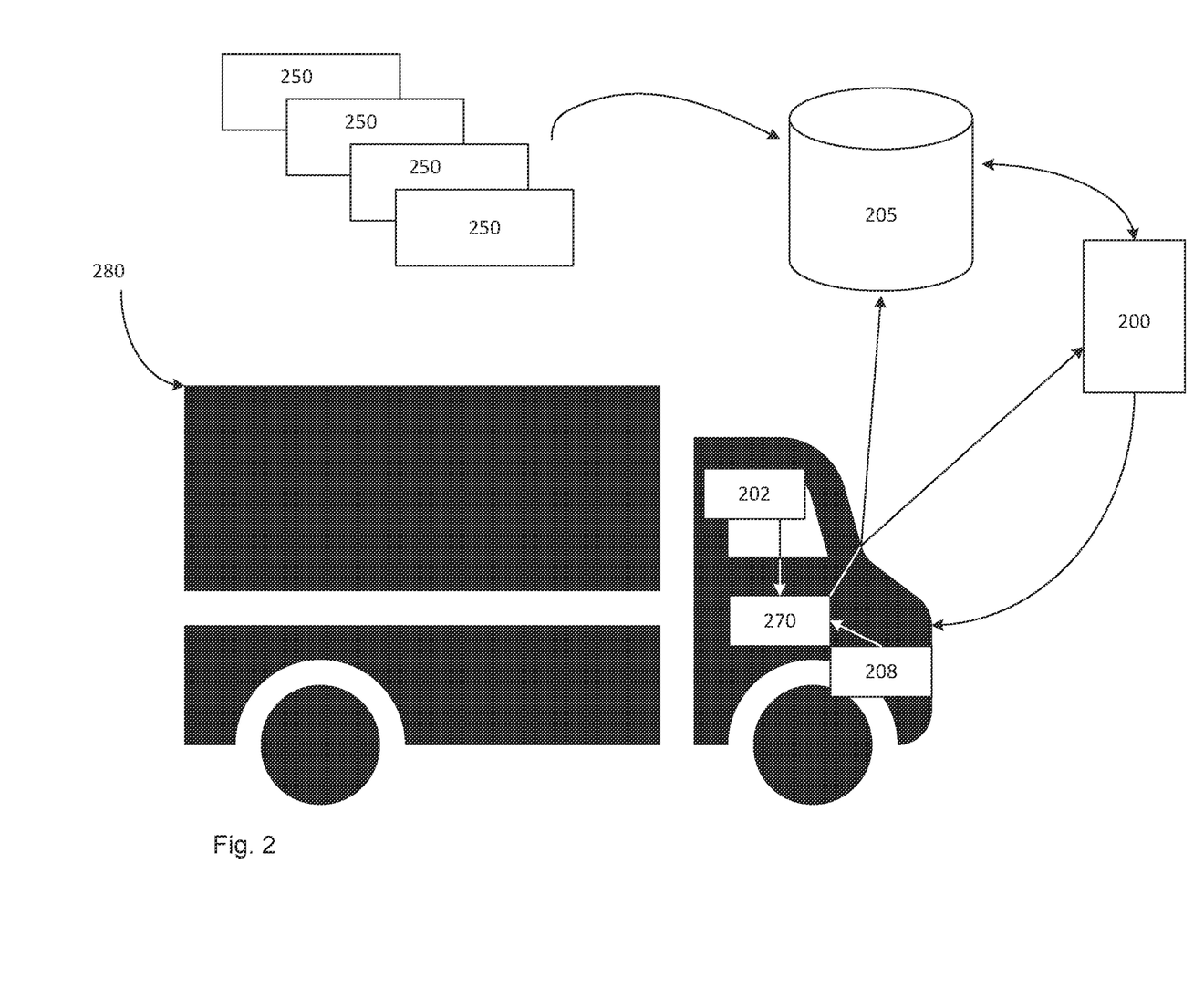
FIG. 2 shows another example of a system for determining the driving condition and state of a driver.

FIG. 2 shows an example of a vehicle 280. The vehicle 280 comprises an electronic unit 270 which receives data obtained from different data sources of the vehicle. The data sources may be a well-being device 202 and one or more steering devices 208 of the vehicle. The electronic unit 270 transmits the received data to a database 205 and to a computing unit 200. Furthermore, the electronic unit 270 may act as a harmonizer for data, whereby the data to be transmitted is already in a commensurable format. According to another embodiment, the data harmonization may take place in the database 205 or in the computing unit 200. Furthermore, the database 205 receives data from one or more external data sources 250. The computing unit 200, which comprises a processor and a computer program stored in a memory, determines the driving behavior index on the basis of data received from the electronic unit 270 of the vehicle, and optionally from the external data sources 250 as well. On the basis of the driving behavior index determined by the computing unit 200, it is possible to control e.g., the control equipment 208 of the vehicle 280. The computing unit 200 may be a part of the database 205, a part of the electronic unit 270, or an independent device. The computing unit 200 is responsible for the functionality of the driving behavior device 100 of FIG. 1.

As an example of the use and the chain of reasoning, the following is presented: The database stores data on a road network, indicating locations where run-off-road accidents have occurred. Furthermore, stored data on the moment of the run-off-road accident is available, such as traffic weather, season of year, time of day, collected at the respective moment from data sources producing such data. Moreover, details of the vehicle run off the road and its driver (speed, acceleration, heart rate, alertness, etc.) are stored. Driver profiles are also stored in the database, wherein at least the driver's age, driving experience and health are recorded. On the basis of history data, the system is capable of determining the conditions under which the run-off-road accident occurred, but also of determining the factors which have influenced on staying on the road under similar conditions.

On the basis of this data, the system makes an analysis of the driving situation at hand. Data on such a driving situation is received, including data on the vehicle, the load of the vehicle, the conditions, the speed, and the location of the vehicle. Further, driver-specific data on the driving situation is received, including data on the heart rate, the moisture of the hands, and the dilation of the pupils of the driver. When, on the basis of the location data, the system detects that the driver is approaching a challenging bend, the speed of the vehicle is relatively high and the pulse of the driver is accelerating, it is possible for the system, on the basis of this data, to rate the driving behavior index at a low level in view of the situation, and to transmit the data not only as information to the driver but also as a speed-limiting control command to the vehicle.

Consequently, on the basis of the analysis made and stored data on driving situations, it is possible to predict the risk level of driving performances. It is thus possible to describe the driver's ability to make decisions and thereby to adjust his/her performance according to the conditions.

For predictions, it is also possible to make a risk analysis for each driving situation on different road sections according to a) the accident history and danger spots of the road section, b) data on the geographical profile and the road network, c) the road and weather condition, d) history data on the driver, etc. Thus, when a given risk level is exceeded, it is possible, for example, to change the route or the driver, and to give instructions on the route, for example when approaching danger spots.

Figure 3:
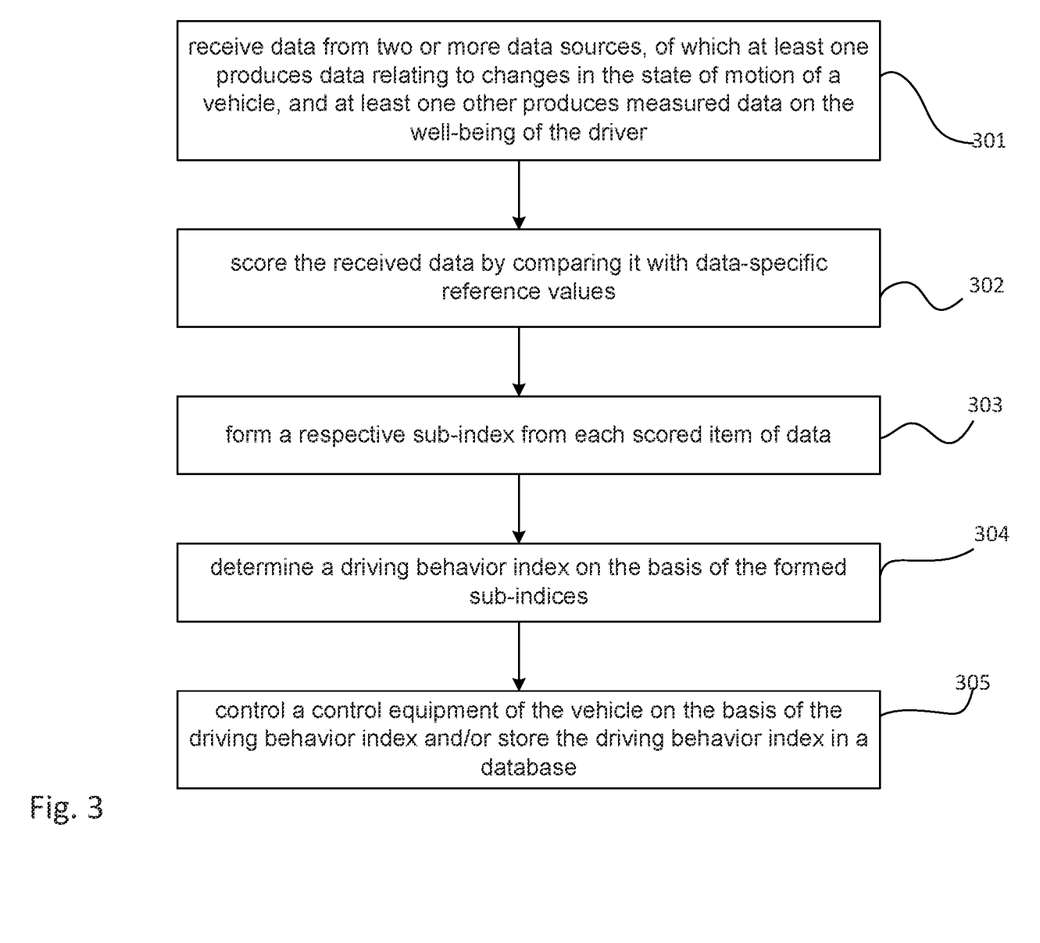
FIG. 3 is a flowchart of a method according to an example.

A method according to an embodiment is illustrated in FIG. 3. The method comprises at least receiving 301 data from two or more data sources, of which at least one produces data relating to changes in the state of motion of a vehicle, and at least one other produces measured data on the well-being of the driver; scoring 302 the received data by comparing it with data-specific reference values; forming 303 a respective sub-index from each scored item of data; determining 304 a driving behavior index on the basis of the formed sub-indices; and controlling 305 a control equipment of the vehicle on the basis of the driving behavior index; and/or storing the driving behavior index in a database. The different steps of the method can be implemented by corresponding hardware and/or software modules in a computer.

A device according to an embodiment comprises means for receiving data from two or more data sources, at least one producing data relating to changes in the state of motion of the vehicle and at least one other generates measured data on the well-being of the driver; means for scoring the received data by comparing it with data-specific reference data; means for forming a related sub-index from each scored item of data; means for determining a driving behavior index on the basis of the formed sub-indices; means for controlling a control equipment of the vehicle on the basis of the driving behavior index and/or for storing the driving behavior index in a database. These means may comprise at least one processor, and a memory comprising a computer program. When executed by said at least one processor, the computer program makes the device perform different steps of the method according to FIG. 3.

A device according to an embodiment is shown in FIG. 4. The device 400 comprises at least one processor 401 and a memory 402. At least a computer program 403 comprising commands executable in a computer is stored in the memory 402. When executed by the processor 401, the commands of the computer program 403 make the device 400 perform the method according to FIG. 3. Furthermore, the device 400 comprises a communication interface 404 configured for communication between the device 400 and an external system. The communication may be wireless and/or wired, as presented above.

It will be obvious that the present invention is not limited solely to the above-presented embodiments but it can be modified within the scope of the appended claims.

The invention claimed is:

1. A device for determining the driving behavior of a driver of a vehicle, the device comprising at least a processor and a memory storing a computer program code, which when executed by the processor, causes the device to:
    receive data from a plurality of data sources, wherein the data comprises at least data relating to changes in the state of motion of the vehicle, data on well-being of the driver being obtained from a well-being device worn by the driver, situational data, and history data;
    score at least the received data relating to changes in the state of motion of the vehicle and data relating to the well-being of the driver by comparing them with data-specific reference values;
    form a respective sub-index from each scored item of data;
    determine a driving behavior index on the basis of the formed sub-indices;
    determine a current driving behavior of the driver based on the determined driving behavior index and a real-time data on the well-being of the driver;
    analyse a current situation based on the situational data;
    determine whether the driving behavior causes a risk in the current situation;
    control a control equipment of the vehicle on the basis of the driving behavior and/or for storing the driving behavior index in a database.

2. The device according to claim 1, wherein the situational data comprises one or more of the following items:
    location data;
    traffic data;
    weather/road condition data.

3. The device according to claim 1, wherein the well-being device is one of the following: a smart watch, a smart ring, a fitness tracker band; and the data on well-being comprises one or more of the following items:
    heart rate data;
    sleep data;
    alertness;
    stress level;
    oxygen saturation;
    activity level;
    body temperature;
    moisture content.

4. The device according to claim 1, comprising a data connection to a starting system of the vehicle for transmitting a start inhibit command on the basis of the driving behavior index.

5. The device according to claim 1, comprising a data connection to a speed control system of the vehicle for transmitting a speed limit command on the basis of the driving behavior index.

6. The device according to claim 1, comprising means for limiting driving in a specific area and/or at a specific time.

7. The device according to claim 1, comprising means for transmitting messages relating to capability to drive to a well-being device, a mobile device and/or an information display of the vehicle.

8. The device according to claim 1, wherein the means for determining the driving behavior index on the basis of the formed sub-indices is configured to determine weighting coefficients for each sub-index on the basis of data obtained from other data sources or on the basis of history data.

9. A method to be executed on a computer, comprising steps of
receiving data from a plurality of data sources, wherein the data comprises at least data relating to changes in the state of motion of a vehicle, data on well-being of a driver being obtained from a well-being device worn by the driver, situational data and history data;
scoring at least the received data relating to changes in the state of motion of the vehicle and data relating to the well-being of the driver by comparing them with data-specific reference values;
forming a respective sub-index from each scored item of data;
determining a driving behavior index on the basis of the formed sub-indices;
determining a current driving behavior of the driver based on the determined driving behavior index and a real-time data on the well-being of the driver;
analysing a current situation based on the situational data;
determining whether the driving behavior index causes a risk in the current situation;
controlling control equipment of the vehicle on the basis of the driving behavior index, and/or storing the driving behavior index in a database.

10. The method according to claim 9, comprising transmitting a start inhibit command to a starting system of the vehicle on the basis of the driving behavior index.

11. The method according to claim 9, comprising transmitting a speed limit command to a speed control system of the vehicle on the basis of the driving behavior index.

12. The method according to claim 9, comprising means for restricting driving in a specific area and/or at a specific time.

13. The method according to claim 9, comprising transmitting messages relating to capability to drive to the well-being device, a mobile device and/or an information display of the vehicle.

14. The method according to claim 9, comprising determining weighting coefficients for each sub-index on the basis of data obtained from other data sources or on the basis of history data.

15. A device for selecting a driver from a database for a certain driving situation, the device comprising at least a processor and a memory storing a computer program code, which when executed by said processor, causes the device to:
receive a set of parameters relating to a driving situation;
determine from a database one or more drivers being associated with a driving behavior index related to said driving situation;
select a driver from said one or more drivers having the best driving behavior index,
wherein the driving behavior index has been determined based on data being received from a plurality of data sources in real-time in previous corresponding driving situation, wherein the data comprises at least data relating to changes in the state of the motion of a vehicle, data measured from a well-being device of the driver, and data on the situational factors and
to store the driving behavior index of the selected driver determined based on data being received from said plurality of data sources in real-time in the driving situation to which the driver was selected for.

* * * * *